US005346905A

United States Patent [19]
Gerster

[11] Patent Number: 5,346,905
[45] Date of Patent: Sep. 13, 1994

[54] 1-SUBSTITUTED 1H-IMIDAZO-[4,5-C]QUINOLIN-4-AMINES

[75] Inventor: John F. Gerster, Woodbury, Minn.

[73] Assignee: Minnesota Mining and Manufacturing Company, St. Paul, Minn.

[21] Appl. No.: 933,408

[22] Filed: Aug. 21, 1992

Related U.S. Application Data

[63] Continuation-in-part of Ser. No. 754,610, Sep. 4, 1991, Pat. No. 5,268,376.

[51] Int. Cl.$^5$ .................. C07D 471/04; A61K 31/44
[52] U.S. Cl. ..................... 514/293; 546/82; 546/143
[58] Field of Search ................. 546/82; 514/293

[56] References Cited
U.S. PATENT DOCUMENTS 4,689,338  8/1987  Gerster .................... 514/293
4,698,348  10/1987 Gerster .................... 514/293
4,929,624  5/1990  Gerster et al. ............ 514/293
4,988,815  1/1991  Andre et al. .............. 546/159

OTHER PUBLICATIONS

Bachman et al., J. Org. Chem. 15, 1278–1284 (1950).
Jain et al., J. Med. Chem. 11, pp. 87–92 (1968).
Baranov et al., Chem. Abs. 85, 94362 (1976).
Berenyi et al., J. Heterocyclic Chem. 18, 1537–1540 (1981).

*Primary Examiner*—Alan L. Rotman
*Attorney, Agent, or Firm*—Gary L. Griswold; Walter N. Kirn; Douglas E. Reedich

[57] ABSTRACT 1-substituted 1H-imidazo[4,5-c]quinolin-4-amines, active as immunomodulators and antiviral agents. Also, intermediates in the preparation of such compounds, pharmaceutical compositions, and pharmacological methods of use.

11 Claims, No Drawings

1-SUBSTITUTED 1H-IMIDAZO-[4,5-C]QUINOLIN-4-AMINES

CROSS REFERENCE TO RELATED APPLICATION

This application is a continuation-in-part of commonly assigned copending U.S. Ser. No. 07/754,610, filed 4 September 1991, now U.S. Pat. No. 5,268,376.

BACKGROUND OF THE INVENTION

1. Field of the Invention

This invention relates to 1H-imidazo[4,5-c]-quinoline compounds. In other aspects, this invention relates to 1H-imidazo[4,5-c]quinolin-4-amines, intermediates for the preparation of such compounds, pharmaceutical compositions containing such compounds, and pharmacological methods of using such compounds.

2. Description of the Related Art

The first reliable report of the 1H-imidazo-[4,5-c]quinoline ring system, Backman et al., J. Org. Chem. 15, 1278–1284 (1950), describes the synthesis of 1-(6-methoxy-8-quinolinyl)-2-methyl-1H-imidazo[4,5-c]-quinoline for possible use as an antimalarial agent. Subsequently, syntheses of various substituted 1H-imidazo[4,5-c]quinolines have been reported. For example, Jain et al., J. Med. Chem. 11, pp. 87–92 (1968), has synthesized the compound 1-[2-(4-piperidyl)ethyl]-1H-imidazo[4,5-c]quinoline as a possible anticonvulsant and cardiovascular agent. Also, Baranov et al., Chem. Abs. 85, 94362 (1976), has reported several 2-oxoimidazo[4,5-c]quinolines, and Berenyi et al., J. Heterocyclic Chem. 18, 1537–1540 (1981), has reported certain 2-oxoimidazo[4,5-c]-quinolines.

Certain antiviral 1H-imidazo[4,5-c]quinolin-4-amines are described in U.S. Pat. No. 4,689,338 (Gerster). These compounds are substituted on the 1-position by alkyl, hydroxyalkyl, acyloxyalkyl, benzyl, phenylethyl or substituted phenylethyl, and at the 2-position with hydrogen, alkyl, benzyl, or substituted benzyl, phenylethyl or phenyl. Furthermore, these compounds are known to induce interferon biosynthesis. Other antiviral 1H-imidazo[4,5-c]quinolin-4-amines, substituted on the 1-position by alkenyl substituents, are described in U.S. Pat. No. 4,929,624 (Gerster).

U.S. Pat. No. 4,698,348 (Gerster) discloses 1H-imidazo[4,5-c]quinolines that are active as bronchodilators, such as 4-substituted 1H-imidazo-[4,5-c]quinolines wherein the 4-substituent is, inter alia, hydrogen, chloro, alkylamino, or dialkylamino, and the 2-substituent is, inter alia, hydroxyalkyl, aminoalkyl, or alkanamidoalkyl. Said patent also discloses 3-amino and 3-nitro quinoline intermediates substituted at the 4-position by hydroxyalkylamino or cyclohexylmethylamino, and 1H-imidazo[4,5-c]quinoline N-oxide intermediates substituted at the 2-position with, inter alia, hydroxyalkyl, aminoalkyl, or alkanamidoalkyl.

DETAILED DESCRIPTION OF THE INVENTION

This invention provides compounds of Formula

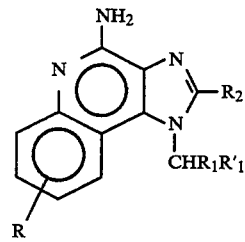

wherein $R'_1$ is hydrogen or a carbon-carbon bond, with the proviso that when $R'_1$ is hydrogen $R_1$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when $R'_1$ is a carbon-carbon bond $R'_1$ and $R_1$ together form a tetrahydrofuranyl group optionally substituted with one or more substituents independently selected from the group consisting of hydroxy and hydroxyalkyl of one to about four carbon atoms;

$R_2$ is selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and R is selected from the group consisting of hydrogen, straight chain or branched chain alkoxy containing one to about four carbon atoms, halogen, and straight chain or branched chain alkyl containing one to about four carbon atoms;

or a pharmaceutically acceptable acid addition salt thereof.

This invention provides intermediate compounds of the formula

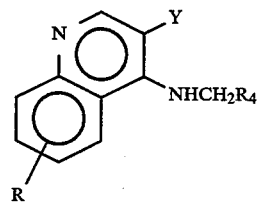

wherein R is as defined above, Y is $-NO_2$ or $-NH_2$, and $R_4$ is alkoxyalkyl wherein the alkoxy moiety contains one to about four carbon atoms and the alkyl moiety contains one to about four carbon atoms.

This invention also provides intermediate compounds of the formula

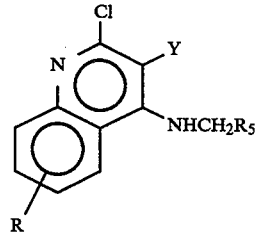

wherein Y and R are as defined above and R₅ is 2-, 3-, or 4-pyridyl.

This invention provides intermediate compounds of the formula

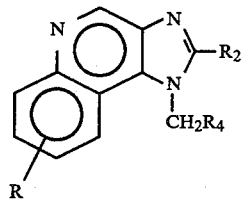

wherein R, R₂, and R₄ are as defined above.

This invention provides intermediate compounds of the formula

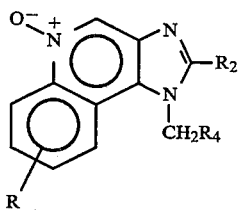

wherein R, R₂, and R₄ are as defined above.

Further this invention provides compounds of the formula

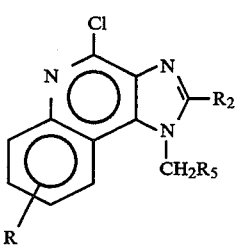

wherein R, R₂, and R₅ are as defined above.

This invention also provides intermediate compounds of the formula

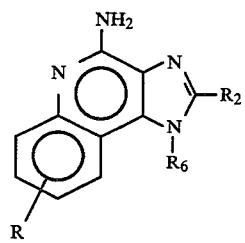

wherein R and R₂ are as defined above and R₆ is alkanoyloxyalkoxy methyl or aroyloxyalkoxy methyl wherein the alkyl group contains one to about four carbon atoms, or tetrahydrofuranyl substituted by one or more substituents independently selected from the group consisting of alkanoyloxy, aroyloxy, and alkanoyloxyalkyl and aroyloxyalkyl wherein the alkyl group contains one to about four carbon atoms.

R₁ of Formula I is preferably alkoxyalkyl or 4-pyridyl.

Other substituents in compounds of Formula I that contain an alkyl radical (e.g., R when R is alkoxy or alkyl) preferably contain two carbon atoms or, more preferably, one carbon atom in each alkyl radical.

It is preferred that R of Formula I be hydrogen.

Preferred compounds of Formula I include: 1-ethoxymethyl-1H-imidazo[4,5-c]quinolin-4-amine; 1-(2-propynyl)-1H-imidazo[4,5-c]quinolin-4-amine; 1-[(tetrahydro-2H-pyran-2-yl)methyl]-1H-imidazo[4,5-c]-quinolin-4-amine; and 1-(2-pyridylmethyl)-1H-imidazo[4,5-c]quinolin-4-amine.

Most preferred compounds of Formula I include 1-(2-methoxypropyl)-2-methyl-1H-imidazo[4,5c]-quinolin-4-amine, 1-(2-methoxyethyl)-2-methyl-1H-imidazo[4,5-c]quinolin-4-amine, and 1-(4-pyridylmethyl)-1H-imidazo[4,5-c]-quinolin-4-amine.

Compounds of Formula I can be prepared by alkylating the 1-position of a 1H-imidazo[4,5-c]-quinolin-4-amine with an alkylating agent of the formula (R'₁)(R₁)HC-X wherein R'₁ and R₁ are as defined above and X is chloro or bromo, in a polar solvent in the presence of sodium hydride. In instances wherein R₁ comprises a hydroxyl group, the hydroxyl group can be protected for the alkylation step and subsequently deprotected. Suitable protecting groups include alkanoyloxy (e.g., acetoxy) or aroyloxy (e.g., benzoyloxy or p-toloyloxy). Reactions for placement and removal of such groups are well known to those skilled in the art and disclosed, e.g., in U.S. Pat. No. 4,689,338 (Gerster), Examples 115-123. 1H-Imidazo-[4,5-c]quinolin-4-amines are disclosed in commonly assigned copending Application Number 07/484,761 (incorporated herein by reference to the extent relevant to the preparation of such compounds) and can be prepared as set forth in Scheme I below:

Scheme I

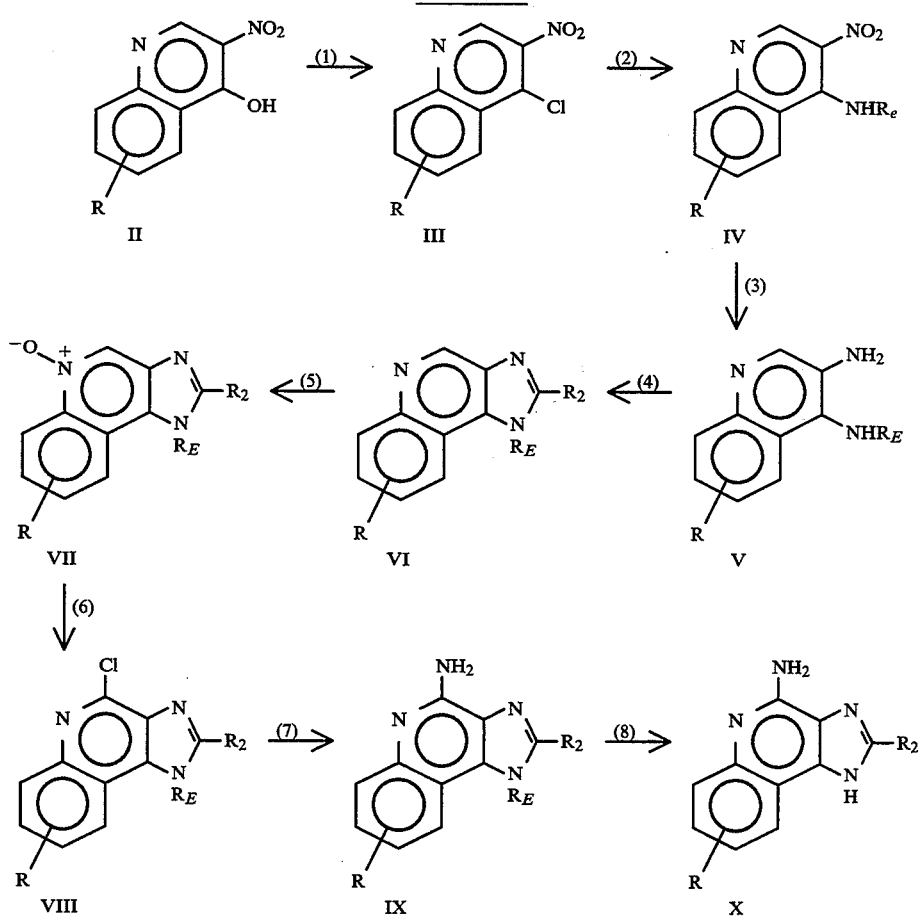

In Scheme I, R and $R_2$ are as defined above and $R_E$ is a substituent capable of being subjected to an elimination or like reaction to afford a 1H-imidazo-[4,5-c]quinolin-4-amine. $R_E$ can be any substituent that can be removed. Examples of general classes of $R_E$ include groups that will yield a stable cation upon treatment with aqueous acid (e.g. tertiary substituents, meaning for the purposes of the instant specification and claims any substituent wherein the carbon atoms bonded to the 1-nitrogen is fully substituted with electron-donating groups, for example hydroxy, alkoxy, acyloxy, halogen, alkyl, phenyl, and the like) and substituents from which the 1H-imidazo[4,5-c]quinolin-4-amine can be eliminated (e.g. 2-hydroxyalkyl groups). Such $R_E$ substituents include 1,1-dimethylethyl (i.e., t-butyl), 1,1-dimethyl-2-hydroxyethyl, 2-hydroxy-1-phenyl-1-methylethyl, 1,1-dimethyl-2-hydroxypropyl, and the like.

Many quinolines of Formula III are known compounds (see, for example, U.S. Pat. No. 3,700,674 and references cited therein). Those that are not known can be prepared by known methods, for example, from 4-hydroxy-3-nitroquinolines as illustrated in step (1) of Scheme I. Step (1) can be conducted by reacting the 4-hydroxy-3-nitroquinoline of Formula II with 1-2 moles of phosphorus oxychloride per mole of the 4-hydroxy-3-nitroquinoline of Formula II. The reaction can be conducted in N,N-dimethylformamide and can be accompanied by heating. In step (2) a 3-nitro-4-chloroquinoline of Formula III is reacted by heating with a compound of the formula $R_ENH_2$, wherein $R_E$ is as defined above, in a suitable solvent such as dichloromethane, water, or tetrahydrofuran, and optionally in the presence of a tertiary amine catalyst such as triethylamine to provide a quinoline of Formula IV.

Steps (1) and (2) can be combined such that the 3-nitro-4-chloroquinoline need not be isolated prior to reaction with $R_ENH_2$. Such a reaction is exemplified in Example 134 and Example 188 (Step A) of U.S. Pat. No. 4,689,338, the disclosure of which is incorporated herein by reference.

A compound of Formula IV is reduced in step (3) preferably using a catalyst such as platinum on charcoal, to provide a compound of Formula V. The reduction can be carried out conveniently on a Paar apparatus in an inert solvent such as toluene or a lower alkanol.

In step (4) an intermediate compound of Formula V is reacted with (i) a 1,1-dialkoxyalkyl alkanoate such as diethoxymethyl acetate, or (ii) a carboxylic acid that will introduce the desired $R_2$ group, or (iii) a trialkyl ortho ester of the formula $R_2C(Oalkyl)_3$, wherein "alkyl" is an alkyl group containing 1 to about 4 carbon atoms, or (iv) a combination of such a carboxylic acid with such a trialkyl ortho ester to provide a compound of Formula VI. The reaction can be carried out by heating, e.g., at about 130° C. in the presence of an acid, preferably an alkanoic acid having one more carbon atom than $R_2$.

Step (5) provides an intermediate of Formula VII. First, the hydroxy group, if one is present in $R_E$, is protected with, for example, an alkanoyloxy group such as acetoxy, or with benzoyloxy. Such protecting groups and reactions for their placement and removal are well known to those skilled in the art. See, for example, U.S. Pat. No. 4,689,338, Examples 115 to 123. The resulting protected compound is then oxidized with a conventional oxidizing agent that is capable of forming N-oxides. Suitable oxidizing agents include peroxyacids and hydrogen peroxide. Heating is generally employed to accelerate the rate of reaction.

In step (6) an N-oxide of Formula VII is first heated in the presence of a suitable chlorinating agent such as phosphorus oxychloride to provide an intermediate of Formula VIII. Phosphorus oxychloride can be used in combination with a solvent (e.g., dichloromethane) inert to conventional chlorinating agents, optionally in the presence of a catalytic amount of N,N-dimethylformamide. The second part of step (6) involves removal of the protecting group, if one is present, by methods well known to those skilled in the art.

In step (7) the 4-chloro group is replaced by a 4-amino group to provide a compound of Formula IX. The intermediate of Formula VIII can be heated, e.g., at 125° to 175 C. under pressure for 6–24 hours in a sealed reactor in the presence of either ammonium hydroxide or a solution of ammonia in an alkanol, (e.g., 15% ammonia in methanol). In step (8), a compound of Formula IX is heated in the presence of aqueous acid to effect the deamination of the $R_E$ group, thus providing a 1H-imidazo[4,5-c]-quinolin-4-amine of Formula X. Preferred conditions for the reaction include brief (e.g., 30 minutes) reflux in dilute (e.g. 4N) aqueous hydrochloric acid.

Another method of preparing compounds of Formula I involves the reactions shown in Scheme II below.

Scheme II

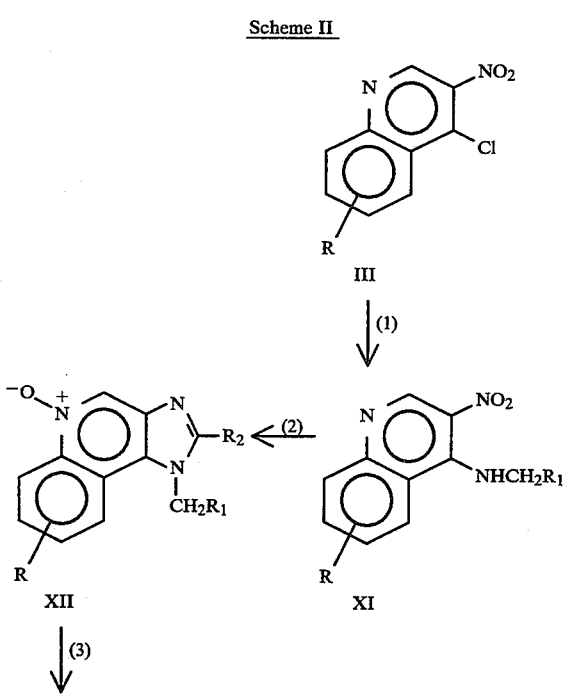

-continued
Scheme II

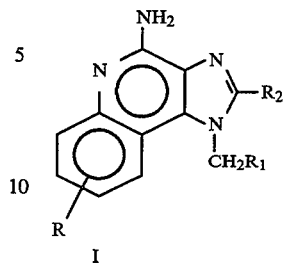

Step 1 of Scheme II involves reacting a compound of Formula III in an inert solvent with an amine of the formula $R_1CH_2NH_2$ to provide a compound of Formula XI. The reaction of step 1 can be carried out in the presence of a tertiary amine catalyst (such as triethylamine).

Step 2 involves: (i) reduction of the nitro group of the compound of Formula XI as described above in connection with step (3) of Scheme I; (ii) reaction of the resulting 3-amino compound with a carboxylic acid or an equivalent thereof as described above in connection with step (4) of Scheme I in order to provide a cyclized imidazo[4,5-c]quinoline; and (iii) oxidizing the quinoline nitrogen as described above in connection with step (5) of Scheme I to provide the N-oxide of Formula XII.

A 1H-imidazo[4,5-c]quinolin-4-amine is prepared in step (3) of the Scheme II. Step (3) involves (i) reacting a compound of Formula XII with an acylating agent; (ii) reacting the product with an aminating agent; and (iii) isolating the compound of Formula I. Part (i) of step (3) involves reacting an N-oxide with an acylating agent. Suitable acylating agents include alkyl- or arylsulfonyl chlorides (e.g., benzenesulfonyl chloride, methanesulfonyl chloride, p-toluenesulfonyl chloride). Arylsulfonyl chlorides are preferred. p-Toluenesulfonyl chloride is most preferred. Part (ii) of step (3) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, and ammonium phosphate). Ammonium hydroxide is preferred. The reaction of step (3) is preferably carried out by dissolving the N-oxide of Formula XII in an inert solvent such as methylene chloride, adding the aminating agent to the solution, and then adding the acylating agent. Preferred conditions involve cooling to about 0° C. to about 5° C. during the addition of the acylating agent. Heating or cooling can be used to control the rate of the reaction.

Compounds of Formula XIX, a subgenus of Formula I, can be prepared according to the general method disclosed in U.S. Pat. No. 4,988,815 (Andre et al.), incorporated herein by reference), as shown below in Scheme III, wherein R and $R_2$ are as defined above and $R_7$ is 1-alkynyl of two to about ten carbon atoms, tetrahydropyranyl alkoxyalkyl wherein the alkoxy moiety contains one to about four carbon atoms and the alkyl moiety contains one to about four carbon atoms, 2-, 3-, or 4-pyridyl.

Scheme III

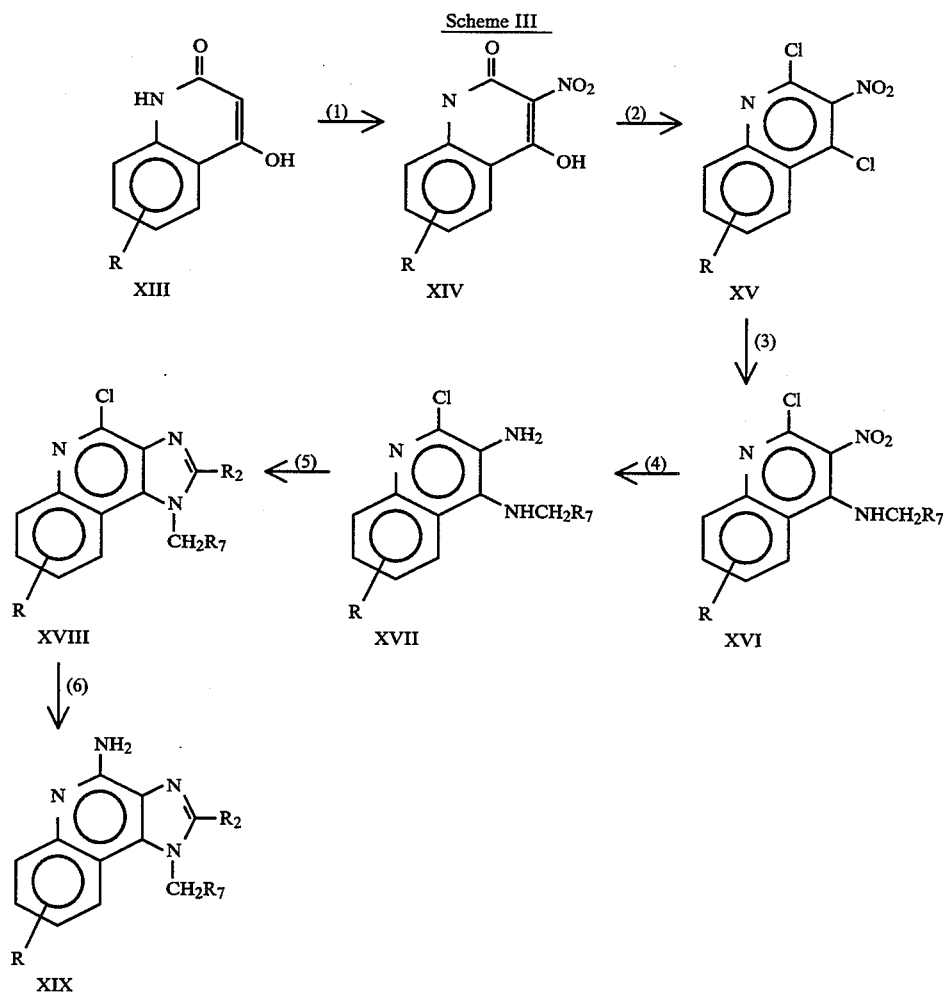

The unsubstituted compound of Formula XIII, 4-hydroxy-2(1H)-quinolinone, is a known, commercially available compound, and other compounds of Formula XIII can be prepared therefrom by methods known to those skilled in the art. For example, Chem. Bet., 1927, 60, 1108 (Kohler), discloses the preparation of 7-chloro-4-hydroxy-2(1H)-quinolinone.

In step (1) a compound of Formula XIII is nitrated at the 3-position using conventional nitration methods. It is known to those skilled in the art, however, that nitration is not necessarily selective. For example, depending on the particular R substituent in a compound of Formula XIII and the particular conditions employed, nitration might occur on the benzo ring of a compound of Formula XIII. Those skilled in the art, however, are able to select appropriate conditions that will afford a compound of Formula XIV. Suitable conditions involve mild heating (e.g., at about 40° C.) with acetic acid as the solvent. The unsubstituted compound of Formula XIV, 4-hydroxy-3-nitro-2(1H)quinoline is known and the preparation thereof is disclosed in Chem. Ber., 1918, 5.1, 1500 (Gabriel), the disclosure of which is incorporated herein by reference.

In step (2) the nitrated compound of Formula XIV is chlorinated with a suitable chlorinating agent such as phosphorus pentachloride or phosphorus oxychloride to provide the dichloride product of Formula XV. The reaction can be carried out in an inert solvent or if appropriate in neat chlorinating agent. Mild heating serves to accelerate the rate of reaction. The unsubstituted compound of Formula XV, 2,4-chloro-3-nitroquinoline, is known and the preparation thereof is disclosed in Gabriel cited above.

The product of Formula XV can be isolated if desired, but steps (2) and (3) can be carried out without isolation of the compound of Formula XV. Such a process involves carrying out the reaction of step (2), careful hydrolysis of unreacted chlorinating agent at a relatively low temperature (e.g., below about 35° C.), separating the organic layer, removing the product of Formula XV from the remaining aqueous layer by extraction with an organic solvent, and using the combined organic extracts as described below in connection with step (3).

In step (3), a compound of Formula XV is substituted at the 4-position by reaction with an excess of a compound of the formula $R_7CH_2NH_2$, wherein $R_7$ is as defined above. It is sometimes necessary to use gentle heating (e.g., 50° C.). This reaction proceeds selectively, affording only the 4-substituted product and no detectable amount of the 2-substituted compound. The reaction is run in a solvent comprising a base such as triethylamine or pyridine. When step (3) is run independent of step (2), the reaction can be carried out in a neat basic solvent such as triethylamine. Gentle heating (e.g., at about 70° C.) is preferred.

In step (4), a compound of Formula XVI is reduced to afford a compound of Formula XVII. This reduction can be carried out by conventional methods such as by electrochemical reduction, by reaction with metals such as zinc, tin, or iron in acid, and by other conventional single step or multi-step methods known to those skilled in the art. Suitable reduction conditions include conventional homogeneous or preferably heterogeneous catalytic hydrogenation conditions. A compound of Formula XVI is suspended or dissolved in a solvent such as ethanol, ethyl acetate, methanol, isopropyl alcohol, or mixtures thereof with acetic acid, in the presence of a suitable heterogeneous hydrogenation catalyst such as a platinum or rhodium on alumina, palladium on carbon, platinum on carbon, or the like under hydrogen pressure (e.g., 1–5 atm) in a steel bomb. Isopropyl alcohol is the preferred solvent.

In step (5), a compound of Formula XVII is reacted with an orthoester or an orthoformate of the formula $R_2C(O-Alkyl)_3$ or a carboxylic acid of the formula $R_2CO_2H$ or a mixture thereof, as described above in connection with step (4) of Scheme I.

In step (6), a compound of Formula XVIII is reacted with ammonia as described above in connection with step (7) of Scheme I to afford a compound of Formula XIX.

Compounds of Formula I can be isolated by the conventional means disclosed in U.S. Pat. No. 4,689,338 (Gerster), such as, for example, removal of the solvent and recrystallization from an appropriate solvent (e.g., N,N-dimethylformamide) or solvent mixture, or by dissolution in an appropriate solvent (such as methanol) and re-precipitation by addition of a second solvent in which the compound is insoluble.

A compound of Formula I can be used as an antiviral agent itself or it can be used in the form of a pharmaceutically acceptable acid-addition salt such as a hydrochloride, dihydrogen sulfate, trihydrogen phosphate, hydrogen nitrate, methanesulfonate or a salt of another pharmaceutically acceptable acid. A pharmaceutically acceptable acid-addition salt of a compound of Formula I can be prepared, generally by reaction of the compound with an equimolar amount of a relatively strong acid, preferably an inorganic acid such as hydrochloric, sulfuric, or phosphoric acid, or an organic acid such as methanesulfonic acid, in a polar solvent. Isolation of the salt is facilitated by the addition of a solvent, such as diethyl ether, in which the salt is insoluble.

A compound of the invention can be formulated for the various routes of administration in a pharmaceutically acceptable vehicle, such as water or polyethylene glycol, along with suitable adjuvants, excipients, and the like. Particular formulations will be easily selected by those skilled in the art. Suitable formulations for topical application include creams, ointments and like formulations known to those skilled in the art. Formulations generally contain less than 10% by weight of a compound of Formula I, preferably about 0.1% to 5% by weight of a compound of Formula I.

The compounds of Formula I exhibit antiviral activity in mammals. They can therefore be used to control viral infections. For example, a compound of Formula I can be used as an agent to control infections in mammals caused by Type II Herpes simplex virus. Compounds of Formula I can also be used to treat a herpes infection by oral, topical, or intraperitoneal administration.

A number of compounds of Formula I were tested and found to induce biosynthesis of interferon in human cells. The test methods and results are set forth below. These results suggest that at least certain compounds of the invention might be useful in treating other diseases such as rheumatoid arthritis, warts, eczema, Hepatitis B, psoriasis, multiple sclerosis, essential thrombocythemia, cancer such as basal cell carcinoma, and other neoplastic diseases.

In the following Examples, all reactions were run with stirring under an atmosphere of dry nitrogen unless otherwise indicated. The particular materials and amounts thereof recited in the Example, as well as other conditions and details, should not be construed to unduly limit the invention.

Example 1

1-Ethoxymethyl-1H-imidazo[4,5-c]quinolin-4-amine

A 0.48 g (0.012 mole) portion of 60% sodium hydride was added to a suspension of 2.0 g (0.011 mole) of 1H-imidazo[4,5-c]quinolin-4-amine in 20 mL of dimethylformamide. The resulting mixture was stirred for about 45 minutes until a solution was obtained. A 1.07 g (0.011 mole) portion of chloromethyl ethyl ether was added to the solution. A precipitate formed immediately. The reaction mixture was stirred at room temperature for one hour. The precipitate was collected, slurried with water then dried to give 1.4 g of a solid which was identified as the 1-isomer by nuclear magnetic resonance spectroscopy. This solid was recrystallized from 150 mL of ethanol to provide 0.86 g of 1-ethoxymethyl-1H-imidazo[4,5-c]quinolin-4-amine, m.p. 255°–261° C. Analysis: Calculated for $C_{13}H_{14}N_4O$: % C, 64.4; % H, 5.8; % N, 23.1; Found: % C, 64.2; % H 5.8, % N 22.8.

Example 2

1-(2-Propynyl)-1H-imidazo[4,5-c]quinolin-4-amine

Using the general method of Example 1, 2.1 g of 1H-imidazo[4,5-c]quinolin-4-amine was reacted with 1.7 g of propargyl bromide to provide 0.4 g of 1-(2-propynyl)-1H-imidazo[4,5-c]quinolin-4-amine, m.p. 220°–222° C. The structure was confirmed by nuclear magnetic resonance spectroscopy. Analysis: Calculated for $C_{13}H_{10}N_4$: % C, 70.3; % H, 4.5; % N, 25.2; Found: % C, 70.5; % H, 4.6; % N, 25.4.

Example 3

1-[(Tetrahydro-2H-pyran-2-yl)methyl]-1H-imidazo[4,5-c]quinolin-4-amine

Using the general method of Example 1, 3.0 g of 1H-imidazo[4,5-c]quinolin-4-amine was reacted with 2-bromomethyltetrahydropyran to provide about 2.5 g of a mixture of the 1 and 3 isomers. The mixture was slurried with about 30 mL of refluxing ethyl acetate then cooled in an ice bath. The resulting precipitate was collected and dried to provide 0.6 g of 1-[(tetrahydro-2H-pyran-2-yl)methyl]-1H-imidazo[4,5-c]quinolin-4-amine, m.p. 206°–210° C. The structure was confirmed by nuclear magnetic resonance spectroscopy. Analysis: Calculated for $C_{16}H_{18}N_4O$: % C, 68.1; % H, 6.4; % N, 19.8; Found: % C, 67.8; % H, 6.4; % N, 19.6.

Example 4

1-[(2-Acetoxyethoxy)methyl]-1H-imidazo[4,5-c]quinolin-4-amine

Using the general method of Example 1, 5.0 g of 1H-imidazo[4,5-c]quinolin-4-amine was reacted with (2-acetoxyethoxy)methyl bromide (prepared according to the method of Robins et al., Can. J. Chem. 60, 547 (1982)) to provide 5.3 g of a yellow solid. The solid was slurried with ethyl acetate to provide 2.3 g of a light yellow solid which was identified as the 1-isomer by nuclear magnetic resonance spectroscopy.

Example 5

1-[(2-Hydroxyethoxy)methyl]-1H-imidazo[4,5-c]quinolin-4-amine

A 2.1 g portion of 1-[(2-acetoxyethoxy)-methyl]-1H-imidazo[4,5-c]quinolin-4-amine was combined with 25 mL of 15% ammonia in methanol and stirred at room temperature for about 16 hours. The resulting precipitate was collected, rinsed with ether and dried to provide 1.1 g of a solid. This solid was recrystallized from 50 mL of ethanol to provide 0.8 g of 1-[(2-hydroxyethoxy)]methyl-1H-imidazo[4,5c]quinolin-4-amine as a yellow crystalline solid, m.p. 210°–212° C. Analysis: Calculated for $C_{13}H_{14}N_4O_2$: % C, 60.4; % H, 5.5; % N, 21.7; Found: % C, 60.3; % H, 5.5; % N, 21.5.

Example 6

1-(2-Deoxy-3,5-di-O-p-toluoyl-D-erythro-pentofuranosyl)-1H-imidazo[4,5-c]quinolin-4-amine A 0.34 g (0,011 mole) portion of 60% sodium hydride was added to a suspension of 1.7 g (0,009 mole) of 1H-imidazo[4,5-c]quinolin-4-amine in 65 mL of methylene chloride. The reaction mixture was then diluted with 65 mL of acetonitrile and stirred at room temperature for 2 hours. 3.6 g (0.009 mole) of 2-deoxy-3,5-di-O-p-toluoyl-D-erythropentosyl chloride (prepared according to the method of Bhat, pp. 521–22 from Volume 1, Synthetic Procedures in Nucleic Acid Chemistry, Zorbach and Tipson (1968)) was added to the reaction mixture and stirring at room temperature was continued for about 16 hours. The reaction mixture was filtered to remove a small amount of insoluble material. The filtrate was evaporated to provide a residue which was purified by silica gel chromatography using ethyl acetate as the eluent to provide 1.4 g of the 3-isomer and 2.0 g of the 1-isomer. The structural assignments were confirmed by nuclear magnetic resonance spectroscopy.

Example 7

1-(2-Deoxy-β-D-erythro-pentofuranosyl)-1H-imidazo[4,5-c]quinolin-4-amine

A 2.2 g portion of 1-(2-deoxy-3,5-di-O-p-toluoyl-D-erythro-pentofuranosyl)-1H-imidazo[4,5-c]-quinolin-4-amine was dissolved in about 150 mL of 15% ammonia in methanol and stirred at room temperature for about 48 hours. The volume of the reaction was reduced to about 50 mL and the precipitate collected to provide 0.56 g of a solid. The filtrate was evaporated and the residue was slurried with ether then filtered to provide 0.55 g of a solid. The two solids were combined then recrystallized from ethanol to provide 0.8 g of 1-(2-deoxy-β-D-erythro-pentofuranosyl)-1H-imidazo[4,5-c]quinolin-4-amine, m.p. 232°–237° C. Analysis: Calculated for $C_{15}H_{16}N_4O_3$: % C, 60.0; % H, 5.4; % N, 18.7; Found: % C, 59.7; % H, 5.4; % N, 18.3.

Example 8

N-(2-Methoxyethyl)-3-nitro-4-quinolinamine

A mixture containing 16 mL (0.22 mole) of thionyl chloride and 18 mL of dimethylformamide was added to a suspension of 38 g (0.2 moles) of 4-hydroxy-3-nitroquinoline in 500 mL of dichloromethane. The resulting mixture was heated at reflux for 2 hours and then allowed to cool to room temperature. A 20 mL (0.23 mole) portion of methoxyethylamine was combined with 30 mL of triethylamine and the combination was slowly added with vigorous stirring to the reaction mixture. A vigorous heat of reaction was observed and the mixture was allowed to reflux until the heat of reaction dissipated. The reaction mixture was concentrated under vacuum to provide a residue which was then slurried with dilute hydrochloric acid. The slurry was filtered and the filtrate was made basic with ammonium hydroxide. The resulting precipitate was collected, rinsed with water and air dried to provide 37.4 g of a yellow solid. A sample of this material was recrystallized from ethanol-dichloromethane to provide N-(2-methoxyethyl)-3-nitro-4-quinolinamine as a yellow solid, m.p. 113°–115° C. Analysis: Calculated for $C_{12}H_{13}N_3O_3$: % C, 58.3; % H, 5.3; % N, 17.0; Found: % C, 58.0; % H, 5.3; % N, 16.8.

Example 9

1-(2-Methoxyethyl)-2-methyl-1H-imidazo[4,5-c]quinoline

A mixture containing 12.5 g of N-(2-methoxyethyl)-3-nitro-4-quinolinamine, 0.6 g of 5% platinum on carbon, 10 g of magnesium sulfate and 380 mL of ethyl acetate was hydrogenated in a Parr apparatus at an initial pressure of about 53 psi. After the hydrogenation was complete, the reaction mixture was filtered. The filtrate was evaporated under vacuum to provide the diamine intermediate as a clear amber oil. The oil was taken up in 150 mL of glacial acetic acid and the resulting solution was refluxed for one and a half hours before being evaporated under vacuum. The resulting residue was dissolved in water. The solution was made strongly basic with aqueous sodium hydroxide then extracted several times with ethyl acetate. The extracts were combined, dried over magnesium sulfate and evaporated. The residue was slurried with ether/hexane then filtered to provide 9.5 g of crude product. A 0.5 g sample was recrystallized to provide pure 1-(2-methoxyethyl)-2-methyl-1H-imidazo[4,5-c]quinoline, m.p. 128°–130° C. Analysis: Calculated for $C_{14}H_{15}N_3O$: % C, 69.7, % H, 6.3; % N, 17.4; Found: % C, 69.8; % H, 6.3; % N, 17.4.

Example 10

1-(2-Methoxyethyl)-2-methyl-1H-imidazo[4,5-c]quinolin-4-amine

A 6.3 mL (0.03 mole) portion of 32% peracetic acid was added to a solution of 7.0 g (0.029 mole) of 1-(2-methoxyethyl)-2-methyl-1H-imidazo[4,5-c]quinoline in 100 mL of ethyl acetate. The solution was heated at reflux for 30 minutes and then allowed to cool to room temperature. The resulting precipitate was collected, rinsed with a small amount of ethyl acetate and dried to provide 7.7 g of the N-oxide as a solid. The N-oxide was dissolved in 125 mL of dichloromethane then mixed with 40 mL of concentrated ammonium hydroxide. The resulting heterogeneous mixture was stirred vigorously and cooled to 4° C. A 5.7 g (0.03 mole) portion of p-toluenesulfonyl chloride was dissolved in 25 mL of dichloromethane and added dropwise to the mixture. The rate of addition was controlled such that the reaction mixture was maintained at a temperature of 4°–9° C. After the addition was completed the reaction mixture was allowed to stir at room temperature for one hour. The dichloromethane was removed under vacuum. The aqueous mixture was diluted further with water and the solid was collected, washed with water and dried to provide 6.1 g of crude product as a tan solid. The tan solid was recrystallized from methanol/dichloromethane to provide 3.0 g of 1-(2-methoxyethyl)-2-methyl-1H-imidazo[4,5-c]quinolin-4-amine as a colorless crystalline solid, m.p. 230°–233° C. Analysis: Calculated for $C_{14}H_{16}N_4O$: % C, 65.6; % H, 6.3; % N, 21.9; Found: % C, 65.5; % H, 6.1; % N, 21.7.

Example 11

2-Chloro-3-nitro-N-(2-pyridylmethyl)-4-quinolinamine

A 8.2 g portion of 2,4-dichloro-3-nitroquinoline was dissolved in 85 mL of dimethylformamide. 2-(Aminomethyl)pyridine (2.5 mL) was added dropwise followed by the addition of 4.7 mL of triethylamine. The reaction mixture was stirred for 15 minutes then an additional 1.0 mL of 2-(aminomethyl)pyridine was added. The reaction mixture was stirred at room temperature for about an hour and then on a steam bath for about 45 minutes. The reaction mixture was diluted with 150 mL of water. The resulting precipitate was collected and dried to provide 7.3 g of a yellow brown solid. The solid was slurried with about 75 mL of refluxing hexane then filtered while hot to give 4.5 g of a solid. A 200 mg sample was recrystallized from about 15 mL of ethanol to provide pure 2-chloro-3-nitro-N-(2-pyridylmethyl)-4-quinolinamine, m.p. 179°–182° C. Analysis: Calculated for $C_{15}ClH_{11}N_4O_2$: % C, 57.2; % H, 3.5; % N, 17.8; Found: % C, 57.4; % H, 3.6; % N, 17.7.

Example 12

2-Chloro-N⁴-(2-pyridylmethyl),3,4-quinolinediamine

A mixture containing 5.8 g of 2-chloro-3-nitro-N-(2-pyridylmethyl)-4-quinolinamine, 5.8 g of magnesium sulfate, 0.6 g of 5% platinum on carbon and 300 mL of ethyl acetate was hydrogenated on a Parr apparatus. After the hydrogenation was complete, the reaction mixture was filtered and the filtrate evaporated to provide 4.6 g of a solid. A sample was recrystallized from ethyl acetate/hexane to provide pure 2-chloro-N4-(2-pyridylmethyl)-3,4-quinolinediamine m.p. 98°–102° C. Analysis: Calculated for $C_{15}ClH_{13}N_4$: % C, 63.3; % H, 4.6; % N, 19.7; Found % C, 63.5; % H, 4.7; % N, 19.8.

Example 13

4-Chloro-1-(2-pyridylmethyl)-1H-imidazo[4,5-c]quinoline

A 1.6 mL portion diethoxymethyl acetate was added to a solution of 2.3 g of 4-Chloro-N⁴-(2-pyridylmethyl)-3,4-quinolinediamine in 15 mL of warm xylene. The reaction mixture was heated on a steam bath for 90 minutes then diluted with hexane. The precipitate was collected and dried to provide 2.3 g of a solid. A 300 mg sample was recrystallized from 10 mL of ethanol to provide pure 4-chloro-1-(2-pyridylmethyl)-1H-imidazo[4,5-c]quinoline, m.p. 217°–220° C. Analysis: Calculated for $C_{16}ClH_{11}N_4$: % C, 65.2; % H, 3.8; % N, 19.0; Found: % C, 65.0; % H, 3.7; % N, 18.8.

Example 14

1-(2-Pyridylmethyl)-1H-imidazo[4,5-c]quinolin-4-amine

A mixture of 2.4 g of 4-chloro-1-(2-pyridyl-methyl)-1H-imidazo[4,5-c]quinoline and 50 mL of 15% ammonia in methanol was placed in a bomb and heated at 150° C. for 6 hours. After cooling, the reaction mixture was filtered. The solid was slurried with aqueous sodium bicarbonate, collected and dried to provide 1.9 g of crude product. The crude product was recrystallized from 350 mL of ethanol to provide 1.25 g of a solid, m.p. 278°–284° C. The mother liquor was concentrated to a volume of 50 mL to provide a second crop of 0.32 g, m.p. 275°–281° C. The two crops were combined for analysis. Analysis: Calculated for $C_{16}H_{13}N_5$: % C, 69.8; % H, 4.8; % N, 25.4; Found % C, 69.7; % H, 4.8; N, 25.2.

Example 15

2-Chloro-3-nitro-N-(4-pyridylmethyl)-4-quinolinamine

Using the general method of Example 11, 6.8 g of 2,4-dichloro-3-nitroquinoline was reacted with 4-(aminomethyl)pyridine to provide 7.8 g of crude 2-chloro-3-nitro-N-(4-pyridylmethyl)-4-quinolinamine. This material was used without further purification.

Example 16

2-Chloro-N⁴-(4-pyridylmethyl)-3,4-quinolinediamine

Using the general method of Example 12, 5.0 g of 2-chloro-3-nitro-N-(4-pyridylmethyl)-4-quinolinamine was hydrogenated to provide 2.9 g of crude 2-chloro-N⁴-(4-pyridylmethyl)-3,4-quinolinediamine. This material was used without further purification.

Example 17

4-Chloro-1-(4-pyridylmethyl)-1H-imidazo-[4,5-c]quinoline

A mixture containing 2.9 g of 2-chloro-N⁴-(4-pyridylmethyl)-3,4-quinolinediamine and 3 mL of diethoxymethyl acetate was heated on a steam bath for about 45 minutes. The reaction suspension was dissolved in cold dilute aqueous hydrochloric acid. The solution was made basic with ammonium hydroxide. The resulting oily solid was taken up in ethyl acetate and purified by silica gel chromatography using first ethyl acetate then 5% methanol in ethyl acetate as the eluent to provide 0.9 g of a solid. A 100 mg portion was recrystallized from 5 mL of ethanol to provide 4-chloro-1-(4-pyridylmethyl)-1H-imidazo[4,5-c]-quinoline, m.p. >300° C. Analysis: Calculated for $C_{16}ClH_{11}N_4$: % C, 65.2; % H, 3.8; % N, 19.0; Found: % C, 64.8; % H, 3.9; % N, 18.5.

Example 18

1-(4-Pyridylmethyl)-1H-imidazo[4,5-c]quinolin-4-amine

Using the general method of Example 14, 0.8 g of 4-chloro-1-(4-pyridylmethyl)-1H-imidazo[4,5-c]quinoline was aminated to provide 0.25 g of 1-(4-pyridylmethyl)-1H-imidazo[4,5-c]quinolin-4-amine, m.p. >300° C. Analysis: Calculated for $C_{16}H_{13}N_5$: % C, 69.8; % H, 4.8; % N, 25.4; Found: % C, 70.2; % H, 4.9; % N, 25.5.

Example 19

Part A

1-[(3-Nitro-4-quinolinyl)amino]-2-propanol

A mixture containing 16 mL (0.22 mole) of thionyl chloride in 18 mL of dimethylformamide was added with stirring to a suspension of 38 g (0.2 mole) of 4-hydroxy-3-nitroquinoline. The resulting mixture was heated at reflux for 3 hours then cooled to −15° C. in a dry ice bath. A solution containing 18 mL (0.23 mole) of 1-amino-2-propanol and 30 mL (0.23 mole) triethylamine in 100 mL of methylene chloride was added dropwise with vigorous stirring to the chilled reaction mixture. After the addition was complete, the reaction mixture was heated at reflux for about 30 minutes. The reaction mixture was concentrated under vacuum to provide a yellow precipitate which was collected, rinsed with water and a small amount of ethanol and dried to provide 45 g of a yellow crystalline solid. A 1 g portion was recrystallized to provide 1-[(3-nitro-4-quinolinyl)amino]-2-propanol as a yellow crystalline solid, m.p. 209°–210° C. The structure was confirmed by nuclear magnetic resonance spectroscopy.

Part B

α,2-Dimethyl-1H-imidazo[4,5-c]quinoline-1-ethanol

Using the general method of Example 9, 44.2 g of 1-[(3-nitro-4-quinolinyl)amino]-2-propanol was hydrogenated to provide the intermediate diamine as a brown oil. Using the general method of Example 9, 17 g of the crude diamine was reacted with glacial acetic acid to provide 6.3 g of crude product. A sample was recrystallized from ether to provide α,2-dimethyl-1H-imidazo[4,5-c]quinoline-1-ethanol as a blue tinged solid, m.p. 176°–177° C. The structure was confirmed by nuclear magnetic resonance spectroscopy.

Part C 1-(2-Methoxypropyl)-2-methyl-1H-imidazo[4,5-c]quinoline

Sodium hydride (1 g of 60%) was added to a suspension of 5 g (0.021 mole) of α,2-dimethyl-1H-imidazo[4,5-c]quinoline-1-ethanol in 100 mL of tetrahydrofuran. The resulting mixture was stirred for an hour. Methyl iodide (1.55 mL; 0.025 mole) was added and the reaction mixture was stirred for an hour. The reaction mixture was diluted with water then extracted three times with ethyl acetate. The ethyl acetate extracts were combined, dried over magnesium sulfate then concentrated under vacuum to provide 4.9 g of crude product as a brown oil. The oil was refluxed for one hour with 250 mL of hexane then filtered. The filtrate was cooled and the resulting precipitate was collected and dried to provide 2.4 g of a sticky light yellow powder. A sample was recrystallized from ether to provide 1-(2-methoxypropyl)-2-methyl-1H-imidazo[4,5-c]quinoline as a white crystalline solid, m.p. 55°–57° C. The structure was confirmed by nuclear magnetic resonance spectroscopy.

Example 20

1-(2-Methoxypropyl)-2-methyl-1H-imidazo[4,5-c]quinoline 5N Oxide

Using the general method of Example 10, 2.4 g of 1-(2-methoxypropyl)-2-methyl-1H-imidazo[4,5-c]quinoline was oxidized using peracetic acid to provide 2.65 g of the crude N oxide as a yellow solid. A 100 mg sample was recrystallized from ethyl acetate to provide 1-(2-methoxypropyl)-2-methyl-1H-imidazo[4,5-c]quinoline 5N oxide as a solid, m.p. 146°–149° C. The structure was confirmed by nuclear magnetic resonance spectroscopy.

Example 21

1-(2-Methoxypropyl)-2-methyl-1H-imidazo[4,5-c]quinolin-4-amine

Using the general method of Example 10, 2.55 g of 1-(2-methoxypropyl)-2-methyl-1H-imidazo[4,5-c]quinoline 5N oxide was aminated to provide 2.5 g of crude product as a light orange powder. The powder was recrystallized from ethyl acetate to provide 1.46 g of 1-(2-methoxypropyl)-2-methyl-1H-imidazo[4,5-c]quinolin-4-amine as a white crystalline solid, m.p. 196°–197° C. Analysis: Calculated for $C_{15}H_{18}N_4O$: % C, 66.6; % H, 6.7; % N, 20.7; Found: % C, 66.4; % H, 6.7; % N, 20.6.

Compounds of the invention were tested according to the test methods set forth below.

ANTIVIRAL ACTIVITY AND INTERFERON INDUCTION IN GUINEA PIGS

The test methods described below demonstrate the ability of compounds of the invention to reduce the number and severity of lesions developed by guinea pigs infected with Type II Herpes simplex virus and to induce the biosynthesis of interferon in guinea pigs, Female Hartley guinea pigs weighing 200 to 250 g are anesthetized with methoxyflurane (available under the tradename METAFANE TM from Pitman-Moore, Inc., Washington Crossing, N.J.), after which the vaginal area is swabbed with a dry cotton swab. The guinea pigs are then infected intravaginally with a cotton swab saturated with Herpes simplex virus Type II strain 333 ($1 \times 10^5$ plaque forming units/mL). Guinea pigs are assigned to groups of 7 animals; one group for each treatment and one to serve as a control (vehicle treated). The compounds of the invention are formulated in water containing 5% Tween 80 (a polyoxyethylene sorbitan monooleate available from Aldrich Chemical Company, Inc., Milwaukee, Wisc.). The guinea pigs are treated orally once daily for four consecutive days starting 24 hours after infection.

Antiviral Activity

Antiviral activity is evaluated by comparing lesion development in compound-treated versus vehicle-treated guinea pigs. External lesions are scored 4, 7, 8 and 9 days after infection using the following scale: 0 - no lesion, 1 - redness and swelling, 2 - a few small vesicles, 3 - several large vesicles, 4 - large ulcers with necrosis and 5 - paralysis. The maximum lesion score of each guinea pig is used to calculate the percentage lesion inhibition. The percentage lesion inhibition is calculated as follows:

$$100 - \left\{ \frac{\text{Sum of maximum lesion scores of treatment group} \times 100}{\text{Sum of maximum lesion scores of control group}} \right\}$$

Interferon Induction

Twenty-four hours after the initial dose of test compound has been administered, blood is obtained from 3 guinea pigs from each treatment group by cardiac puncture of methoxyflurane anesthetized animals. Blood is pooled and allowed to clot at room temperature. After low speed centrifugation, serum is collected and stored at −70° C. until analysis.

Interferon levels in the guinea pig serum are determined in a standard microtiter assay using transformed guinea pig cells (ATCC CRL 1405). The interferon assay is done in 96 well microtiter plates. Confluent monolayers of transformed guinea pig cells are treated with dilutions of guinea pig serum made with medium 199 (GIBCO, Grand Island, N.Y.). The cell and serum dilutions are incubated at 37° C. overnight. The following day, the medium and serum are removed and about 10 plaque forming units of Mengovirus are added to each well. Controls consist of wells that receive no guinea pig serum (virus positive control) and wells that receive no virus (virus negative control). Cells and virus are incubated for 2 to 3 days at 37° C. before quantifying for viral cytopathic effect. The viral cytopathic effect is quantified by staining with 0.05% crystal violet followed by spectrophotometric absorbance measurements. The titer of interferon in serum is expressed as units/mL and is the reciprocal of the highest dilution that protects cells from virus.

Results are shown in the table below.

Antiviral Activity and Interferon Induction in Guinea Pigs

| Compound of Example | Dose mg/kg | % Lesion Inhibition | Reference Units/mL |
|---|---|---|---|
| 1 | 2 | 55% | not determined |
| 2 | 2 | 57% | 600 |
| 14 | 2 | 20% | not determined |
| 18 | 2 | 0% | not determined |
| 18 | 5 | 88% | >12,800 |

These results show that the tested compounds of the invention inhibit Herpes simplex virus type II lesions in guinea pigs. Those compounds tested were also shown to induce interferon biosynthesis in guinea pigs.

INTERFERON-α INDUCTION IN HUMAN CELLS

The test methods described below demonstrate the ability of compounds of the invention to induce the biosynthesis of interferon-α in human cells.

An in vitro human blood cell system was used to assess interferon-e induction by compounds of the invention. Activity is based on the measurement of interferon secreted into culture medium. Interferon is measured by bioassay.

Blood Cell Preparation for Culture

Whole blood is collected by venipuncture into EDTA vacutainer tubes. Peripheral blood mononuclear cells (PBM's) are prepared by LeucoPREP TM Brand Cell Separation Tubes (available from Becton Dickinson) and cultured in RPMI 1640 medium (available from GIBCO, Grand Island, N.Y.) containing 25 mM HEPES 4-(2-hydroxyethylpiperazine-N'-2-ethanesulfonic acid and L-glutamine (1% penicillin-streptomycin solution added) with 10% autologous serum added. Alternatively, whole blood diluted 1:10 with RPMI 1640 medium supplemented with 25 mM HEPES and L-glutamine with 1% penicillin-streptomycin solution added can be used. 200 μL portions of diluted whole blood or of PBM in medium are added to 96 well (flat bottom) MicroTest TM III tissue culture plates.

Compound Preparation

The compounds are solubilized in water, ethanol, or dimethyl sulfoxide then diluted with distilled water, 0.01N sodium hydroxide or 0.01N hydrochloric acid. (The choice of solvent will depend on the chemical characteristics of the compound being tested.)

Incubation

The solution of test compound is added (in a volume less than or equal to 50 μL) to the wells containing 200 μL of PBM in medium or diluted whole blood. Solvent and/or medium is added to control wells (i.e., wells with no test compound) and also as needed to adjust the final volume of each well to 250 μL. The plates are covered with plastic lids, vortexed gently and then incubated for 24 hours at 37° C. with a 5% carbon dioxide atmosphere.

Separation

Following incubation, the plates are covered with PARAFILM TM and then centrifuged at 1000 rpm for 15 minutes at 4° C. in a Damon IEC Model CRU-5000 centrifuge. Medium (about 175 μL) is removed from 4 to 8 wells and pooled into 2 mL sterile freezing vials. Samples are maintained at −70° C. until analysis.

Interferon Analysis/Calculation

Interferon is determined by bioassay using A549 human lung carcinoma cells challenged with encephalomyocarditis. The details of the bioassay method are described by G. L. Brennan and L. H. Kronenberg in "Automated Bioassay of Interferons in Micro-test Plates" Biotechniques, June/July; 78, 1983., incorporated herein by reference. Briefly stated the method is as follows: interferon dilutions and A549 cells are incubated at 37° C. for 12 to 24 hours. The incubated cells are infected with an inoculum of encephalomyocarditis virus. The infected cells are incubated for an additional period at 37° C. before quantifying for viral cytopathic effect. The viral cytopathic effect is quantified by staining followed by spectrophotometric absorbance measurements. Results are expressed as α interferon reference units/mL based on the value obtained for NIH HU IF-L standard. The interferon was identified as essentially all interferon alpha by testing in checkerboard neutralization assays against rabbit anti-human interferon (beta) and goat anti-human interferon (alpha) using A549 cell monolayers challenged with encephalomyocarditis virus. Results are shown in the table below wherein the absence of an entry indicates that the compound was not tested at the particular dose concentration. Results designated as "<" a certain number indicate that interferon was not detectable in amounts above the lower sensitivity level of the assay.

| Compound of Example | Interferon-Induction in Human Cells Reference Units/mL Dose Concentration (μg/mL) | | | | | | | | Cell Type |
|---|---|---|---|---|---|---|---|---|---|
| | 0.01 | 0.05 | 0.10 | 0.50 | 1.0 | 2.5 | 5.0 | 10 | |
| 1 | * | * | * | * | 210 | * | 630 | 360 | whole blood |
| 2 | * | * | * | 21 | * | 190 | 110 | * | whole blood |
| 3 | * | * | * | 110 | * | 140 | 64 | * | whole blood |
| 5 | * | * | * | * | 1.8 | * | 84 | 190 | whole blood |
| 7 | * | * | <1.8 | <1.8 | <1.8 | * | 84 | * | PBM |
| 10 | <4 | 24 | 3300 | 1600 | 490 | * | 490 | * | PBM |
| 14 | <1 | <1 | <1 | <1 | 570 | * | 430 | * | PBM |
| 18 | <1 | <1 | <1 | 430 | 330 | * | 430 | * | PBM |
| 21 | <4.5 | 160 | 830 | 830 | 830 | * | 710 | * | PBM |

*not determined

These results show that the tested compounds of the invention induce interferon biosynthesis at detectable levels in human whole blood and/or PBM cells over a wide range of dose concentrations.

What is claimed is:

1. A compound of the formula:

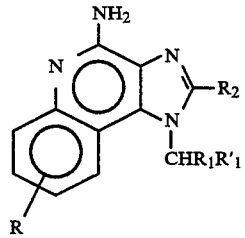

wherein $R'_1$ is hydrogen and $R_1$ is 2-, 3-, or 4-pyridyl; $R_2$ is selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and R is selected from the group consisting of hydrogen, straight chain or branched chain alkoxy containing one to about four carbon atoms, halogen, and straight chain or branched chain alkyl containing one to about four carbon atoms;

or a pharmaceutically acceptable acid addition salt thereof.

2. A compound according to claim 1, wherein $R_2$ is hydrogen.

3. A compound according to claim 1, wherein R is hydrogen.

4. A compound according to claim 1, wherein $R_2$ is alkyl of one to about four carbon atoms.

5. A compound according to claim 1, wherein $R_2$ is hydrogen.

6. A compound according to claim 1, wherein $R_2$ is alkyl of one to about four carbon atoms.

7. The compound 1-(2-pyridylmethyl)-1H-imidazo[4,5-c]quinolin-4-amine according to claim 1.

8. The compound 1-(4-pyridylmethyl)-1H-imidazo[4,5-c]quinolin-4-amine according to claim 1.

9. A method of inducing interferon biosynthesis in a mammal, which method comprises administering to the mammal a compound according to claim 1 in an amount sufficient to induce interferon biosynthesis.

10. An antiviral pharmaceutical composition comprising a compound according to claim 1 and a pharmaceutically acceptable vehicle, the compound being present in an amount effective to inhibit or prevent the progress of a herpes simplex II infection.

11. A method of treating a herpes simplex II infection comprising the step of administering a compound according to claim 1 in an amount effective to inhibit or prevent the progress of the herpes simplex II infection.

* * * * *

UNITED STATES PATENT AND TRADEMARK OFFICE
CERTIFICATE OF CORRECTION

PATENT NO. : 5,346,905
DATED : September 13, 1994
INVENTOR(S) : John F. Gerster

It is certified that error appears in the above-indentified patent and that said Letters Patent is hereby corrected as shown below:

Col. 1, line 67, after "formula" insert --I:--.

Cols. 5 & 6, in Scheme I, formula IV, "NHR$_e$" should be --NHR$_E$--.

Col. 5, line 46, "atoms" should be --atom--.

Col. 9, line 44, "Bet.," should be --Ber.,--.

Col. 9, line 61, "5.1" should be --51,--.

Col. 13, line 27, "(0,009" should be --(0.009--.

Col. 15, line 44, "2-chloro-N4-(2-" should be --2-chloro-N$^4$-(2- --.

Col. 16, line 11, the second occurrence of "N," should be --%N,--.

Col. 18, line 33, "105" should be --10$^5$--.

Col. 19, line 52, "interferon-e" should be --interferon-α--.

Signed and Sealed this

Fourth Day of April, 1995

*Attest:*

BRUCE LEHMAN

*Attesting Officer*    *Commissioner of Patents and Trademarks*